United States Patent
Wiese et al.

(10) Patent No.: US 11,341,609 B2
(45) Date of Patent: May 24, 2022

(54) METHOD AND SYSTEM FOR GENERATING A PANORAMIC IMAGE

(71) Applicant: 3SHAPE A/S, Copenhagen K (DK)

(72) Inventors: Ole P. Wiese, Brønshøj (DK); Thomas Sangild Sørensen, Aarhus C (DK)

( * ) Notice: Subject to any disclaimer, the term of this patent is extended or adjusted under 35 U.S.C. 154(b) by 0 days.

(21) Appl. No.: 16/651,815

(22) PCT Filed: Sep. 28, 2018

(86) PCT No.: PCT/EP2018/076484
§ 371 (c)(1),
(2) Date: Mar. 27, 2020

(87) PCT Pub. No.: WO2019/063797
PCT Pub. Date: Apr. 4, 2019

(65) Prior Publication Data
US 2020/0234404 A1 Jul. 23, 2020

(30) Foreign Application Priority Data
Sep. 28, 2017 (DK) .............................. PA201770733

(51) Int. Cl.
*G06T 3/40* (2006.01)
*G06T 7/11* (2017.01)
(Continued)

(52) U.S. Cl.
CPC .............. *G06T 3/4038* (2013.01); *A61B 6/03* (2013.01); *A61B 6/145* (2013.01); *A61B 6/4085* (2013.01);
(Continued)

(58) Field of Classification Search
CPC ..... G06T 7/11; G06T 7/13; G06T 7/20; G06T 7/70; G06T 2207/10081;
(Continued)

(56) References Cited

U.S. PATENT DOCUMENTS

| 8,503,604 B2* | 8/2013 | Inglese | ................... A61B 6/14 378/40 |
| 10,076,291 B2 | 9/2018 | Arai et al. | |

(Continued)

FOREIGN PATENT DOCUMENTS

| JP | 2013135842 A | 7/2013 | |
| WO | WO-2016156150 A1 * | 10/2016 | ............... A61B 6/14 |

OTHER PUBLICATIONS

Baan et al. "Fusion of intra-oral scans in cone-beam computed tomography scans." Clinical Oral Investigations 25.1 (2020): 77-85. (Year: 2020).*

(Continued)

*Primary Examiner* — Katrina R Fujita
(74) *Attorney, Agent, or Firm* — Buchanan Ingersoll & Rooney PC

(57) ABSTRACT

A method for generating a panoramic image of a patient includes obtaining a digital 3D surface representation of at least a part of the patient's teeth; using the obtained digital 3D surface representation to define a customized path following the arch form of the patient's teeth; obtaining a plurality of x-ray images of at least a part of one of the patient's jaws and/or teeth; and generating the panoramic image of the patient using the customized path.

9 Claims, 5 Drawing Sheets

(51) Int. Cl.
  *G06T 7/13* (2017.01)
  *G06T 7/70* (2017.01)
  *A61B 6/03* (2006.01)
  *A61B 6/14* (2006.01)
  *A61B 6/00* (2006.01)
  *G06T 7/20* (2017.01)

(52) U.S. Cl.
  CPC ............. *A61B 6/5223* (2013.01); *G06T 7/11* (2017.01); *G06T 7/13* (2017.01); *G06T 7/20* (2013.01); *G06T 7/70* (2017.01); *G06T 2207/10081* (2013.01); *G06T 2207/10116* (2013.01); *G06T 2207/30036* (2013.01); *G06T 2207/30241* (2013.01)

(58) Field of Classification Search
  CPC . G06T 2207/10116; G06T 2207/30036; G06T 2207/30241; A61B 6/03; A61B 6/145; A61B 6/4085; A61B 6/5223
  See application file for complete search history.

(56) References Cited

U.S. PATENT DOCUMENTS

| | | | |
|---|---|---|---|
| 2006/0203959 | A1 | 9/2006 | Spartiotis et al. |
| 2008/0232539 | A1* | 9/2008 | Pasini .................... G06T 19/00 378/4 |
| 2009/0187393 | A1* | 7/2009 | Van Lierde .......... A61C 9/0053 703/11 |
| 2009/0316966 | A1* | 12/2009 | Marshall ............. A61B 6/5217 382/128 |
| 2013/0022252 | A1 | 1/2013 | Chen et al. |
| 2014/0287379 | A1* | 9/2014 | Chun ................... A61C 9/0006 433/42 |
| 2016/0151026 | A1 | 6/2016 | Shibasaki et al. |
| 2016/0275679 | A1 | 9/2016 | Im et al. |
| 2017/0273654 | A1 | 9/2017 | Taguchi et al. |
| 2017/0367792 | A1* | 12/2017 | Raby ...................... A61C 7/20 |
| 2018/0085084 | A1* | 3/2018 | Ojelund ................ A61B 6/542 |
| 2018/0338735 | A1* | 11/2018 | Kim ...................... A61B 6/032 |
| 2019/0175314 | A1* | 6/2019 | Lagardere ............ A61C 9/006 |

OTHER PUBLICATIONS

A. Suomalainen et al., "Dentomaxillofacial Imaging with Panoramic Views and Cone Beam CT", Insights Imaging, 2015, pp. 1-16, vol. 6, doi:10.1007/s13244-014-0379-4.

R. Pauwels et al., "Future Prospects for Dental Cone Beam CT Imaging", Imaging in Medicine, pp. 551-563, vol. 4, No. 5, Oct. 1, 2012.

R. Pauwels et al., "Technical Aspects of Dental CBCT: State of the Art", Dentomaxillofacial Radiology, pp. 1-20, vol. 44, No. 1, Jan. 1, 2015.

The Danish Search Report dated Feb. 14, 2018, by the Danish Patent Office in corresponding Danish Application No. PA 201770733. (6 pages).

* cited by examiner

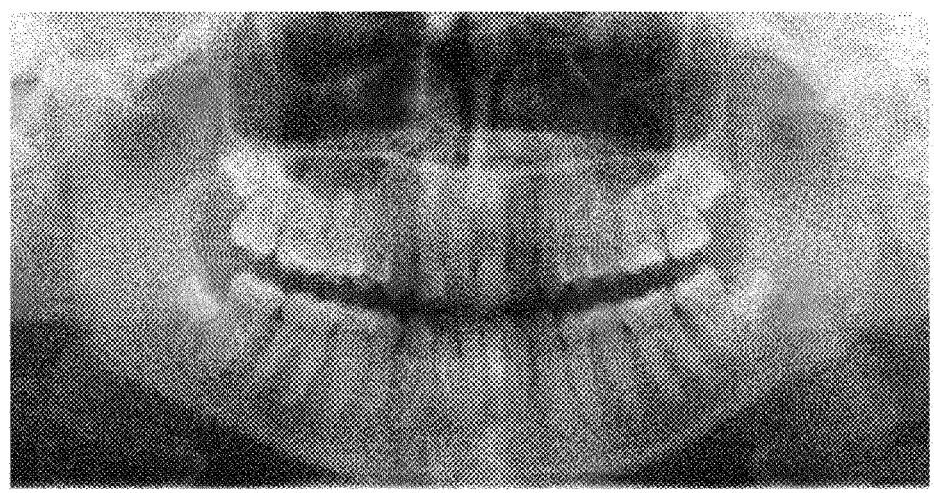
Fig. 1
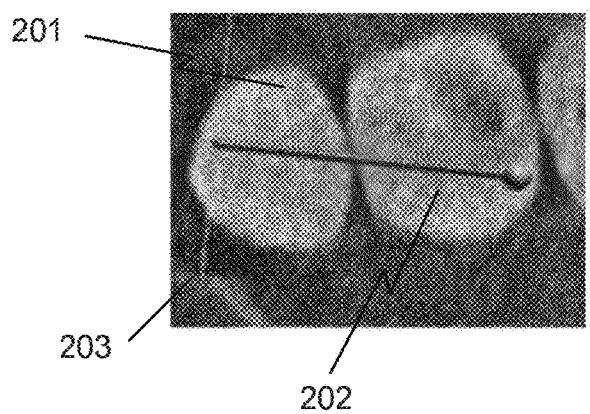
Fig. 2a
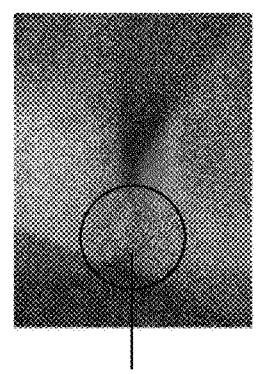
204
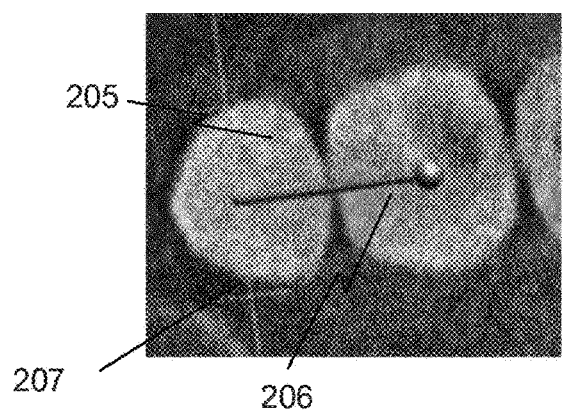
Fig. 2b
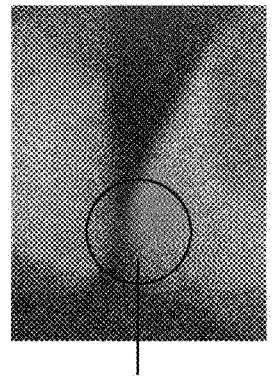
208

METHOD AND SYSTEM FOR GENERATING A PANORAMIC IMAGE

FIELD OF THE INVENTION

This invention generally relates to a system and method for generating a panoramic image. In particular, it relates to generating a dental panoramic image of a patients' teeth and jaws using a cone beam computed tomography scanner.

BACKGROUND OF THE INVENTION

Dental radiographs are commonly called x-rays. Radiographs are used by dentists to find hidden dental structures, malignant or benign masses, bone loss, cavities and other potential problems in a patient's teeth and jaws.

X-ray radiation is sent from an x-ray source, and the x-rays penetrate the various oral structures at different levels depending on anatomical densities, before hitting the analog film or digital sensor.

A traditional dental panoramic radiograph, is an x-ray image which uses a dose of ionizing radiation to capture the entire mouth in one image. Other names for a panoramic radiograph include pantomogram, orthopantomogram, PAN, DPR, OPT, OP and OPG. This typically includes the teeth, maxilla and mandible (upper and lower jaws), as well as the surrounding tissues. However, images may also be taken of only the Temporomandibular Joint (TMJ), only the right or left side of the patient etc. The term "panoramic image" as used in this disclosure, is used as an umbrella term for all of the above Unlike traditional dental x-rays, in which the film or x-ray sensor is placed inside the mouth of the patient, for example using a bitewing, in a panoramic image, the film or x-ray sensor is placed outside of the patient's mouth as part of the x-ray machine.

A panoramic x-ray machine has an x-ray source and sensor mounted 180° degrees from each other on a movable ring. The source and sensor move around the head of the patient, and the radiation which is not absorbed by the patient, is then projected onto the film or sensor.

The traditional panoramic technique is based on the principle of narrow-beam rotational tomograph, uses linked motion between the x-ray source and sensor, where the X-ray beam is angled upward at approximately 8° Because of the nature of this technique, only structures located within the tomographic plane are well defined and those in front or behind that plane tend to be blurry. The tomographic plane, also called the image layer, is shaped like a horseshoe. Objects located inside the image layer will appear wider and objects located in front of it will appear narrower. Theoretically only objects located in the central region of the image layer are depicted sharply and undistorted on the final image. When looking outside the central plane of the image layer, the difference in the horizontal and vertical magnification is responsible for the distortion, with the vertical magnification being smaller. Overlapping of the premolars cannot be avoided in the standard panoramic program because of the anatomy of the jaws.

Distortion and overlapping are the reasons why the horizontal measurements are unreliable on panoramic images. Some modern panoramic devices offer a multilayer panoramic program, increasing the thickness of the focal area compared to traditional panoramic imaging. This decreases patient positioning errors and aids in difficult malocclusion cases.

Panoramic images are used to diagnose conditions such as periodontal disease, cysts in the jaws, cancer, impacted teeth such as wisdom teeth, sinusitis, jaw disorders and others. Panoramic images may also be used in the planning of orthodontic treatment, such as braces and aligners.

A drawback with the traditional panoramic images, are that it requires a relatively high dose of ionizing x-ray radiation, and the traditional panoramic system is a dedicated system used only for this purpose.

Computed tomography scans in dentistry are becoming more common, especially the use of cone beam computed tomography (CBCT). The CBCT scanner is used to acquire 3D digital representations of volumes of a patient's teeth, jaws and surrounding bone and hard tissue. This gives the dentist the opportunity to investigate, diagnose and plan the patient's treatment in 3D.

However, many dentists would still like to have the 2D panoramic image giving a full overview in a single image, so many CBCT systems include a separate imaging mode, in which the CBCT system is used to acquire 2D panoramic image.

In this imaging mode, several thousand x-ray images are taken from different angles, and reconstructed to form the panoramic image.

However, it remains a problem to acquire a panoramic image from a CBCT scanner in which the trajectory of the x-rays around the patient are configured so that the sensor has the same distance to the TMJ and/or the teeth during the whole exposure.

SUMMARY OF THE INVENTION

In one aspect there is disclosed a method for generating a panoramic image of a patient, the method comprising:
  obtaining a digital 3D surface representation of at least a part of the patient's teeth;
  using the obtained digital 3D surface representation to define a customized path following the arch form of the patient's teeth;
  obtaining a plurality of x-ray images of at least a part of one of the patient's jaws and/or teeth; and
  generating the panoramic image of the patient using the customized path.

Accordingly, since a digital 3D surface representation of the patient's teeth is used to define a customized path that follows the arch of the patient's teeth, this means that the resulting panoramic image will be optimized for the actual geometry of the patient's teeth, rather than a standard geometry.

In some embodiments, the customized path is used to define the movement of a medical imaging system during imaging.

The medical imaging system could for example be a standard panoramic imaging system traditionally used in the dental industry, or it could be a CBCT system. Since the customized path is used to define the movement of the imaging system during imaging, the movement of the imaging system can be optimized to give a clearer panoramic image based on the physical geometry of the patient.

In some embodiments, generating the panoramic image of the patient comprises using the obtained x-ray images to reconstruct the panoramic image during post-processing based on the customized path.

In modern digital panoramic imaging systems, up to several thousand x-ray images are taken from different angles and used to reconstruct the panoramic image. Using a patient specific customized path to reconstruct the panoramic image during post-processing will result in a sharper image, giving the dentist a more accurate view of the patient's situation.

In some embodiments the digital 3D surface representation of the patient's teeth is segmented, so that the position and/or outline of each tooth is determined.

By segmenting the digital 3D surface representation, computer algorithms may be used to automatically determine the optimal path.

In some embodiments, the customized path is defined by the position of the molars, premolars, canines and/or the incisors. Preferably, the customized path follows the centre line of the molars and premolars, and the inside edge of the incisors and anterior teeth. By defining the customized path based on the position of the patient's teeth, the resulting panoramic image will more accurately reflect the patient's situation. By having the customized path follow within a short distance range around the centre line of the molars and premolars, and the inside edge of the incisors and anterior teeth, the resulting panoramic image will be the most optimal. The accuracy of the short distance range may be dependent on the physical characteristics of the imaging system, and/or the reconstruction algorithm. Typically, the distance range should be as small as possible, such as less than ±0.1 mm, ±0.2 mm, ±0.5 mm, +1 mm, ±2 mm or ±5 mm.

In some embodiments, the digital 3D surface representation is obtained using an intra-oral scanner.

Using an intra-oral scanner such as the TRIOS by 3Shape to obtain the digital 3D surface representation will give a highly accurate and fast determination of the patient's oral situation. In some instances, the dentist may have already taken a digital impression using an intra-oral scanner at a previous visit, and this may be used to define the customized path.

In some embodiments, the medical imaging system is a CBCT system.

The medical imaging system used for generating the panoramic image may be a traditional digital panoramic imaging system. However, the conventional digital panoramic systems are limited to this application. Therefore, it is an advantage for a dentist to be able to use a CBCT system which also has the ability to for example create an undistorted 3D digital representation of the patient's sub-surface structures. Using the CBCT system in these embodiments means that the dentist needs less equipment in the clinic.

In some embodiments, the initial position of the patient in the CBCT scanner is fixated using a bitetrack.

In some embodiments, the position of the patient in the CBCT scanner is determined using positioning lasers.

It is important to be able to correlate the position of the patient with respect to the CBCT scanner with the previously obtained digital 3D surface representation. Since the patient is at least partially fixated using the bitetrack, and the position of the patient is determined using positioning lasers, it is possible to correlate the position of the patient during the x-ray imaging with the digital 3D surface representation.

BRIEF DESCRIPTION OF THE DRAWINGS

The above and/or additional objects, features and advantages of the present invention, will be further described by the following illustrative and non-limiting detailed description of embodiments of the present invention, with reference to the appended drawings, wherein:

FIG. 1 shows a dental panoramic image.

FIG. 2a shows a closeup of a section of a panoramic image taken with a suboptimal path of the imaging system.

FIG. 2b shows a closeup of a section of a panoramic image taken with an optimal path of the imaging system.

DETAILED DESCRIPTION

Figure 3:
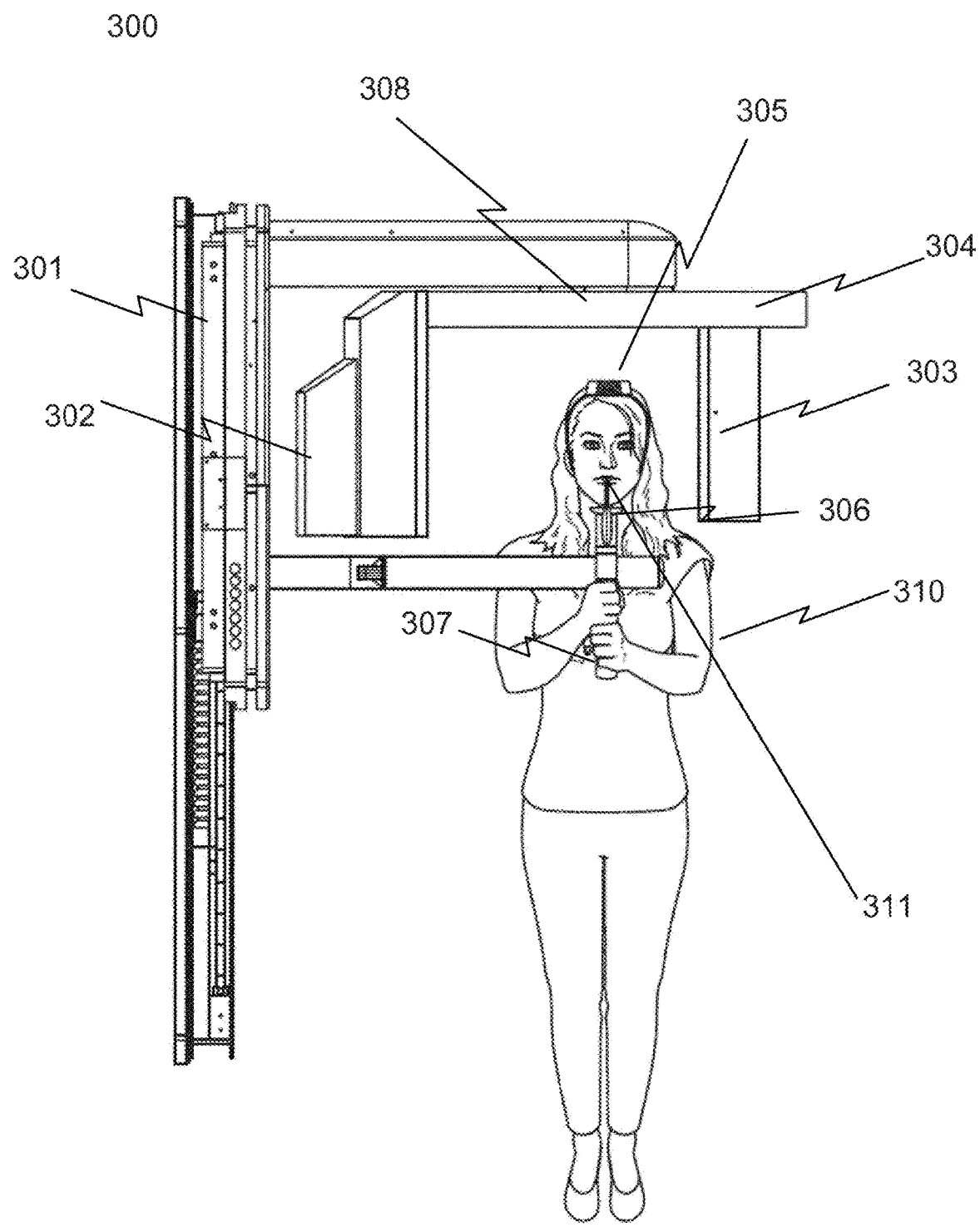
FIG. 3 shows a CBCT system suitable for acquiring a panoramic image.

FIG. 1 shows a panoramic image, showing the patient's teeth 100, upper jaw 101 and lower jaw 102. This image can be used by the dentist to get an overview of the patient's teeth and bone structures.

An embodiment of the method disclosed herein is shown in FIGS. 2a and 2b.

FIG. 2a shows a cross section of a patient's teeth 201, with the path of the x-ray system 202 outlined. Since no adjustment of the path of the system around the head of the patient has been made, and/or no account has been made of the actual physical geometry of the patient's jaws, in this case due to the geometry of the patient's teeth and jaws, the focus plane of the resulting panoramic image does not pass through the center of each of the teeth. The direction of the path of the x-rays is illustrated with the line 203.

The resulting section of the panoramic image is shown to the right in FIG. 2a, where the result of the non-optimal path can be seen. There is an overlap 204 between the teeth which is not seen in the cross section of the patient's teeth.

In other words, because a standard path of the x-ray source and sensor around the head of the patient has been used, the resulting panoramic image is sub-optimal. The same result could be seen in a case where no account has been made of the actual physical geometry of the patient's jaws during the post-processing. Due to the overlap, it will be difficult for the dentist to diagnose any problems occurring in this area.

Turning now to FIG. 2b, the same cross section of the patient's teeth 205 is shown. Here, the path of the scanning system 206 has been customized to the patient's teeth, so that the x-ray path 207 is orthogonal to the surfaces of the teeth. The resulting section of the panoramic image shows that the overlap between the teeth 208 has been eliminated. Therefore the dentist now can see more clearly if there are any problems near the surfaces of the teeth that were overlapping in the previous panoramic image. The same result could be seen if the actual physical geometry of the patient's jaws is used to define the path for post-processing reconstruction, or due to a combination of both the path of the imaging system around the head of the patient as well as post-processing.

FIG. 3 shows a front view of a CBCT scanning system suitable for using the invention disclosed herein. The scanning system comprises a scanner base structure 301, which may be attached to a wall. The scanning system further comprises a radiation source 302, a radiation sensor 303, the radiation source and sensor being attached to or part of a movable ring 304. An optional tracking element 305 is attached to the patient being scanned 310. The scanning system may also comprise a chin rest 306 and a handle 307. In some embodiments, the scanner may comprise a bitetrack 311, a small plate that the patient bites onto in order to fixate the patient's position. The scanner base 301 also comprises at least one camera 308, placed so that it has a clear view of the tracking element 305. The camera(s) 308 are attached to the movable ring 304, so that the camera(s) are in a fixed spatial relationship with the radiation sensor 303 and/or radiation source 302. An integrated or external computer processor (not shown) may also be considered a part of the scanning system.

The radiation source 302 and sensor 303 are located opposite each other and attached to the movable ring 304. In addition to the movement of the source 302 and sensor 303 being able to move with the ring 304, the ring 304 itself can move in two directions in the plane of the ring, thereby making it possible to change the effective angle of the incident x-rays with respect to the patient's teeth.

In some embodiments, it is possible to change the orientation of the emitted x-rays by rotational and/or translational movement of the x-ray source. In this way it is possible to change the effective angle of the incident x-rays with respect to the patient's teeth.

In some embodiments, it is possible to change the orientation of the emitted x-rays by adjusting a collimator placed in front of the x-ray source, to only allow x-rays at a given angle to be emitted.

Figure 4:
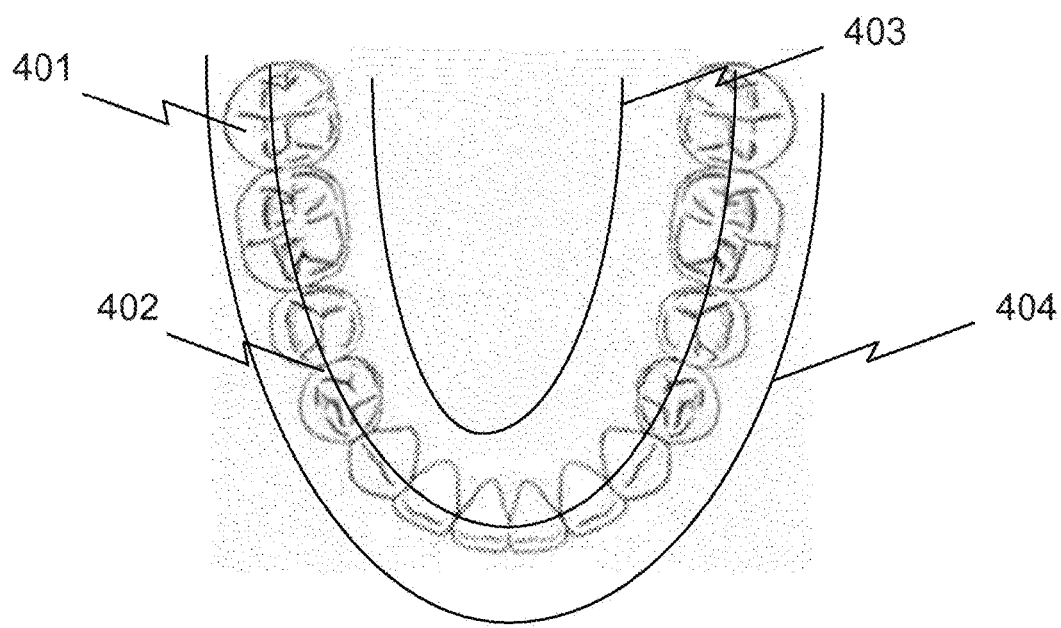
FIG. 4 shows a prior art method for selecting the path of the imaging system.

FIG. 4 shows a prior art way of allowing a user to select the path of a panoramic system. A stylized tooth set 401 is shown, with a standard path of the imaging apparatus outlined 402. The option is then given to the operator to choose a narrower path 403, suitable for example for a child. It may also be possible to choose a wider path 404, suitable for patients with larger jaws.

Figure 5A:
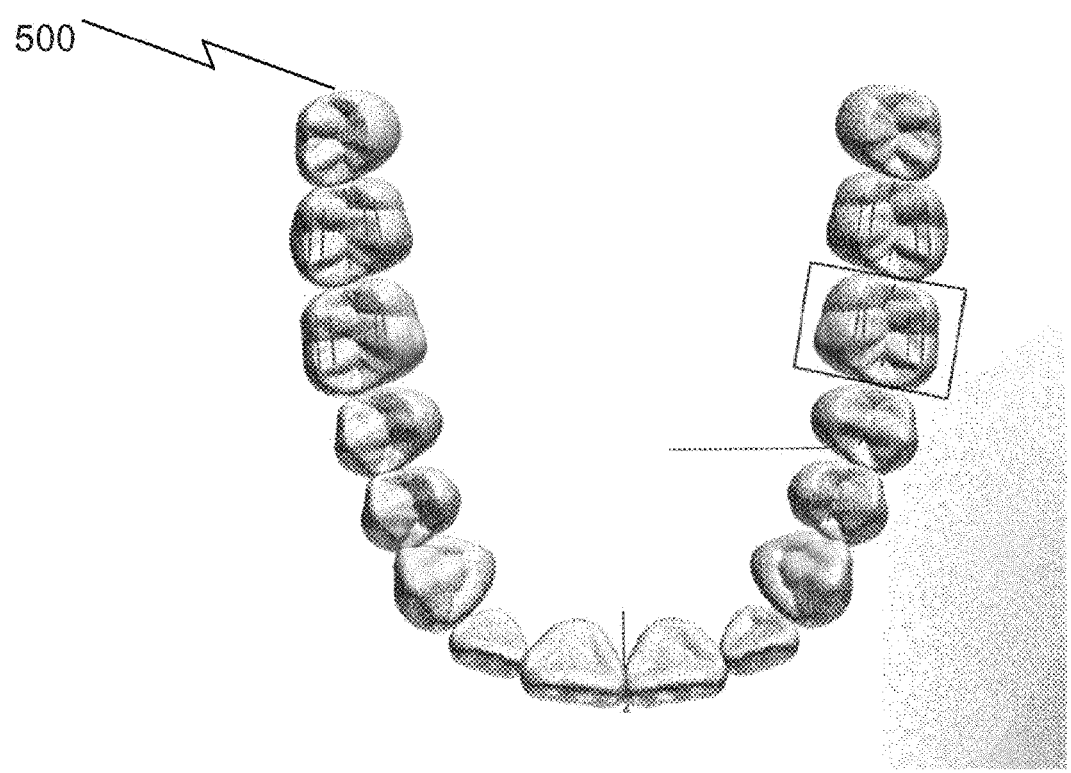
FIG. 5a shows a digital 3D surface representation of the jaw of a patient.
Figure 5B:
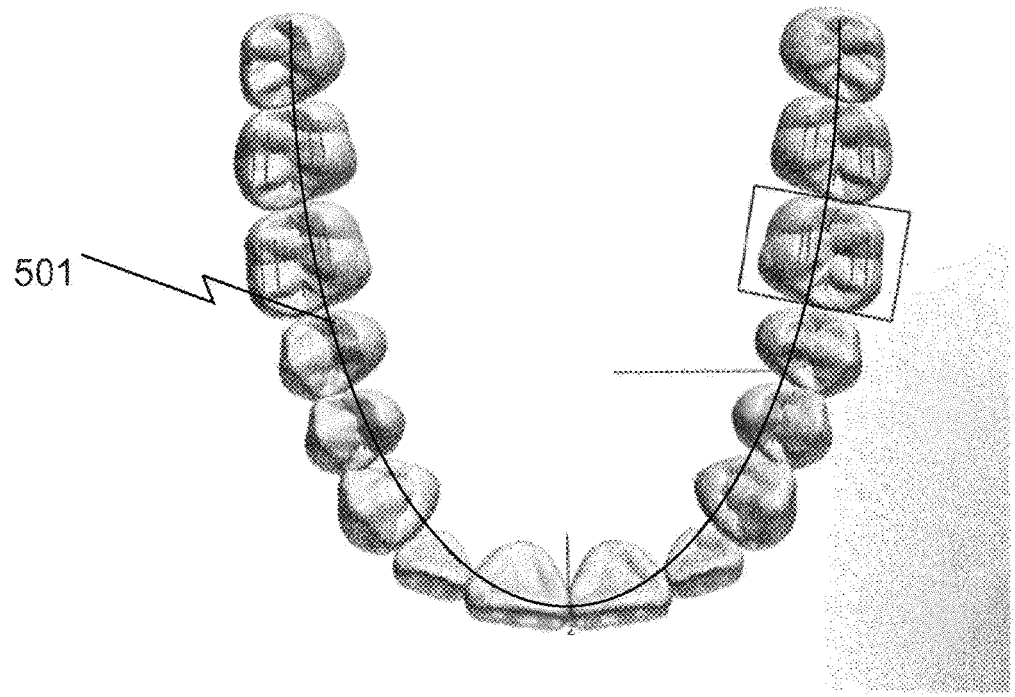
FIG. 5b shows the digital 3D surface representation of the jaw of the patient with the customized path.

FIG. 5 shows an embodiment of the invention as disclosed herein. In FIG. 5a, a digital 3D surface representation of the patient's upper or lower jaw is displayed. The digital representation may have been obtained through several means. For example through conventional means such as an impression scanned directly in a 3D scanner or first making a gypsum model based on the impression, and scanning the gypsum model in the 3D scanner. The digital 3D surface representation may also be a digital impression taken using an intraoral scanner such as the 3Shape Trios. The operator may then manually mark the customized path 501 of the imaging system using a graphical user interface. Alternatively, the customized path may be automatically determined by the computer processing unit. The customized path will normally be chosen to follow the centre line of the molars and the pre-molars, and follow the inside edge of the incisors and anterior teeth. This is due to the fact that the roots of the molars and pre-molars are normally substantially straight, and the roots of the incisors, canines and anterior teeth are normally angled towards the lingual side. Therefore, since the dentist will normally need to see the roots of the teeth as well as possible in a panoramic image, the roots will be more visible in the panoramic image if the optimized path used for the reconstruction follows the inside edge of the incisors and anterior teeth.

During the scanning of the patient, thousands of narrow x-ray images are taken of the patient from various angles. After the raw data has been obtained, it is sent to a computer, where the raw data is manipulated. Here, a trajectory in space is defined, that defines the average TMJ and/or tooth-line. For every point on this line (which is a curved surface when a height co-ordinate is added), all the x-ray images are processed. For each image, the position of the x-ray tube and sensor is known. If a line in 3D from the tube through a specific pixel in the panoramic image intersects the sensor, then this value will be counted for the given pixel. In this way, every pixel of the final reconstructed panoramic image is the sum of up to hundreds or thousands of individual measurements taken from different angles. By summing the measured values, the wanted trajectory can be kept in focus, whereas structures far away from this trajectory will only be present in a limited number of projections, and therefore will be suppressed when summing over many angles. By using a patient specific digital 3D surface representation to define the wanted path, the most accurate, patient specific focus plane can be determined and used in the post-processing. Also, the patient specific path can be used in combination with the post-processing above or alone, to make the actual physical trajectory of the x-ray system during imaging move according to the patient specific path, thereby getting more accurate results.

Figure 6:
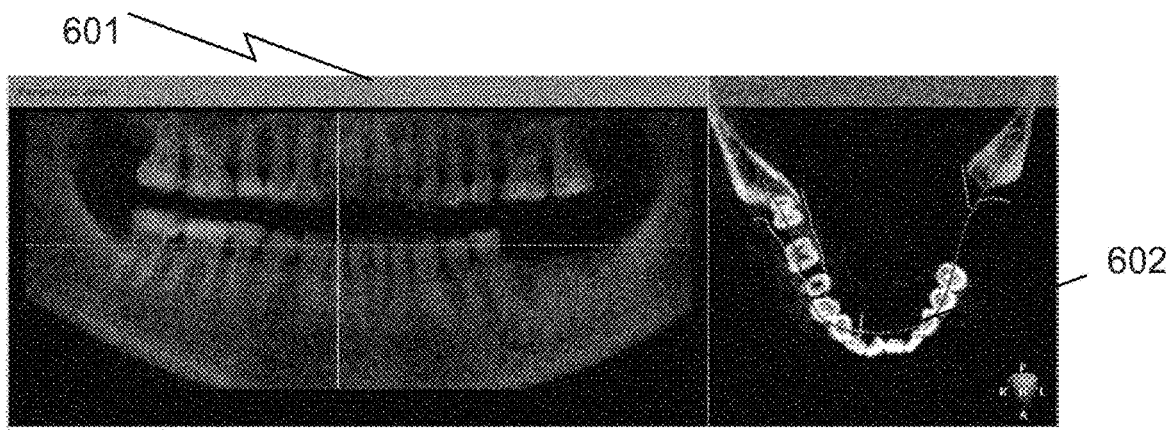
FIG. 6 shows a panoramic image reconstructed using a suboptimal path.

FIG. 6 shows a panoramic image 601 resulting from using a suboptimal path 602 during the reconstruction. As can be seen in the panoramic image, the roots of the anterior teeth are quite blurry and difficult to see, since the focus plane at the position of the anterior teeth has been defined poorly.

Figure 7:
FIG. 7 shows a panoramic image reconstructed using an optimal path.

FIG. 7 shows a panoramic image 701 resulting from using a more optimal path 702 during the reconstruction. As can be seen in the panoramic image, the roots of the anterior teeth are much clearer, since the focus plane at the position of the anterior teeth has been defined taking into account the patient specific digital 3D surface representation.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

The term "obtaining" as used in this specification may refer to physically acquiring for example medical images using a medical imaging device, but it may also refer for example to loading into a computer an image or a digital representation previously acquired.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A method for generating a panoramic image of a patient having jaws and teeth having an arch form, the method comprising:
    obtaining a digital 3D surface representation of at least a part of the patient's teeth using an intraoral scanner, scanning an impression with a 3D scanner, or scanning a gypsum model made from an impression;

using the obtained digital 3D surface representation to define a customized path following the arch form of the patient's teeth;

obtaining a plurality of x-ray images of at least a part of one of the patient's jaws or teeth; and generating the panoramic image of the patient using the customized path;

wherein generating the panoramic image of the patient comprises using the obtained x-ray images to reconstruct the panoramic image during post-processing based on the customized path.

2. The method according to claim 1, wherein the customized path is used to define movement of a medical imaging system during imaging.

3. The method according to claim 1, wherein the customized path is defined by a position of the molars, premolars, canines or incisors.

4. The method according to claim 3, wherein the customized path follows a centre line of the molars and premolars, and an inside edge of the incisors and anterior teeth.

5. The method according to claim 1, wherein the digital 3D surface representation of the patient's teeth is segmented, so that a position or outline of each tooth is determined.

6. The method according to claim 1, wherein the digital 3D surface representation is obtained using an intra-oral scanner.

7. The method according to claim 1, wherein the medical imaging system is a CBCT system.

8. The method according to claim 1, wherein an initial position of the patient in the CBCT scanner is fixated using a bitetrack.

9. The method according to claim 1, wherein a position of the patient in the CBCT scanner is determined using positioning lasers.

* * * * *